United States Patent
Kajii et al.

(10) Patent No.: US 8,916,225 B2
(45) Date of Patent: Dec. 23, 2014

(54) METHOD FOR COATING INNER SURFACE OF MEDICAL TUBE MADE FROM VINYL CHLORIDE WITH ANTI-THROMBOTIC MATERIAL

(75) Inventors: Fumihiko Kajii, Ohtsu (JP); Hidenori Tanaka, Ohtsu (JP); Susumu Kashiwabara, Yokkaichi (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 132 days.

(21) Appl. No.: 13/520,414

(22) PCT Filed: Jan. 6, 2011

(86) PCT No.: PCT/JP2011/050083
§ 371 (c)(1),
(2), (4) Date: Jul. 3, 2012

(87) PCT Pub. No.: WO2011/083815
PCT Pub. Date: Jul. 14, 2011

(65) Prior Publication Data
US 2012/0283665 A1 Nov. 8, 2012

(30) Foreign Application Priority Data
Jan. 7, 2010 (JP) .................................. 2010-001650

(51) Int. Cl.
*A61L 33/00* (2006.01)
*A61L 27/50* (2006.01)
(Continued)

(52) U.S. Cl.
CPC ............... *A61L 27/502* (2013.01); *A61L 27/34* (2013.01); *A61L 29/085* (2013.01); *A61L 29/141* (2013.01); *A61L 31/10* (2013.01); *A61L 31/141* (2013.01); *A61L 33/0052* (2013.01); *A61L 33/068* (2013.01)

USPC .......... 427/2.1; 427/2.24; 427/2.25; 427/230; 427/235

(58) Field of Classification Search
USPC ......................................... 427/2.1, 2.24, 2.25
See application file for complete search history.

(56) References Cited

U.S. PATENT DOCUMENTS 2,867,544 A * 1/1959 Hall, Jr. ..................... 427/235
4,627,844 A 12/1986 Schmitt
(Continued)

FOREIGN PATENT DOCUMENTS

JP 61-113456 A 5/1986
JP 11-035605 A 2/1999
(Continued)

OTHER PUBLICATIONS

International Search Report of PCT/JP2011/050083, mailing date Feb. 22, 2011.
(Continued)

*Primary Examiner* — Dah-Wei D Yuan
*Assistant Examiner* — Andrew Bowman
(74) *Attorney, Agent, or Firm* — Westerman, Hattori, Daniels & Adrian, LLP

(57) ABSTRACT

The present invention provides a method for coating an inner surface of a polyvinyl chloride medical tube containing a plasticizer with an antithrombogenic material composed of a specific (meth)acrylate copolymer. The simple method of the present invention is capable of evenly and efficiently coating an inner surface of a polyvinyl chloride medical tube with a sufficient amount of an antithrombogenic material without causing appearance deterioration or uneven coating due to elution of the plasticizer. The method is performed by passing through a tube a solution that is prepared by dissolving an antithrombogenic material in a solvent composed of water and at least one alcohol that is adjusted to dissolve the copolymer of the antithrombogenic material but does not dissolve the plasticizer, then subsequently passing water through the tube, and finally drying the tube.

6 Claims, 2 Drawing Sheets

(51) Int. Cl.
*A61L 27/34* (2006.01)
*A61L 29/08* (2006.01)
*A61L 29/14* (2006.01)
*A61L 31/10* (2006.01)
*A61L 31/14* (2006.01)
*A61L 33/06* (2006.01)

(56) References Cited

U.S. PATENT DOCUMENTS

| | | | |
|---|---|---|---|
| 4,664,658 A | | 5/1987 | Sawada et al. |
| 4,726,960 A | | 2/1988 | Sawada et al. |
| 4,999,210 A | * | 3/1991 | Solomon et al. ............ 427/2.25 |

FOREIGN PATENT DOCUMENTS

| | | |
|---|---|---|
| JP | 11-164882 A | 6/1999 |
| JP | 11-287802 A | 10/1999 |
| JP | 2002-105136 A | 4/2002 |
| JP | 2002-282356 A | 10/2002 |
| JP | 2007-146133 A | 6/2007 |
| JP | 2007-197686 A | 8/2007 |
| JP | 2008-264266 A | 11/2008 |
| JP | 2008-264719 A | 11/2008 |
| JP | 2008-289864 A | 12/2008 |
| JP | 2009-261437 A | 11/2009 |
| JP | 2009261437 * 11/2009 | .............. A61L 33/00 |

OTHER PUBLICATIONS

Andrade, J.D. et al., "Surfaces and Blood Compatibility", Transactions of American Society of Artificial Internal Organs, 1987, vol. XXXIII, pp. 75-84.

Takemoto, Kiichi et al., "Polymer and Medical Treatment", Mita Shuppan-kai, 1989, pp. 72-73; w/partial English translation.

Matsuda, T. et al. Artificial Organs, 1987, vol. 16 No. 2, pp. 1045-1050; w/partial English translation.

* cited by examiner

METHOD FOR COATING INNER SURFACE OF MEDICAL TUBE MADE FROM VINYL CHLORIDE WITH ANTI-THROMBOTIC MATERIAL

TECHNICAL FIELD

The present invention relates to a method for coating an inner surface of a polyvinyl chloride medical tube containing a plasticizer with an antithrombogenic material composed of a specific (meth)acrylate copolymer. The present invention particularly relates to a method for evenly and efficiently coating an inner surface of a polyvinyl chloride medical tube with a sufficient amount of an antithrombogenic material without causing appearance deterioration or uneven coating due to elution of the plasticizer.

BACKGROUND ART

With its transparency, mechanical strength, and flexibility, polyvinyl chloride has been frequently used for the materials of medical tubes. Usually, a plasticizer, such as DEHP (diethylhexylphthalate), is incorporated in a polyvinyl chloride medical tube to impart flexibility. However, when the polyvinyl chloride tube comes in contact with blood or body fluids, the plasticizer is eluted from the tube. Such elution is considered problematic because it raises concerns including the influence of the eluted plasticizer on a living body and hardening of the tube over time. Meanwhile, there have been attempts regarding surface treatments of medical tubes in order to improve blood compatibility; however, it is difficult to surface-treat the medical tubes, considering the large amount of plasticizer in the tube.

To address these problems, plasticizer-free tube materials composed of an elastomer, tube materials composed of polybutadiene less likely to adsorb medicaments, and the like have been developed. However, these tube materials are inferior in kinking resistance compared with polyvinyl chloride tubes, and therefore break easily. Further, tubes composed of polyolefin materials such as polyethylene have a large impact resilience, which often decreases operability. Further, studies of ethylene-vinyl acetate copolymer, styrene-based elastomer and the like have also been conducted; however, the material costs are significantly higher for these materials than polyvinyl chloride.

On the other hand, there also have been attempts to solve the above problem using a multilayer structure of polyvinyl chloride and polyolefin materials. For example, Patent Document 1 discloses a multilayer tube comprising at least two layers, which includes a chlorinated polyethylene layer as an outer layer and a polyethylene resin layer as an inner layer. Kinking and warping of this multilayer tube do not occur when it is folded, the tube also has moderate flexibility, and there is no change in shape or size after sterilization. With such characteristics, this multilayer tube enables solvent welding with another tube having a different diameter or with injection-molded parts. However, because of the high production costs compared with the materials containing only polyvinyl chloride, this multilayer tube is not widely used.

Further, Patent Document 2 discloses a tri-layered tube comprising a vinyl chloride resin in the outer layer, a low-density polyethylene in the inner layer, and an ethylene-vinyl acetate copolymer in the adhesive layer. Because of the incorporation of a low-density polyethylene in the inner layer, this tri-layered tube is capable of solvent welding and is superior in flexibility. However, this multilayer tube is also not widely used because of the high production costs compared with the materials containing only polyvinyl chloride.

In recent years, there have been active studies of medical devices using various polymer materials, and the use of polymer materials is expected for blood filters, films for artificial kidneys, films for plasma skimming, catheters, films for artificial lungs, artificial blood vessels, films for preventing adhesion, artificial skin, and the like. In these uses, medical devices must have biocompatibility because artificial materials, which are foreign objects for the body, are brought into contact with body tissues and blood. When medical devices are used as a material that comes in contact with blood, (a) prevention of the blood coagulation system, (b) prevention of adhesion/activation of platelets, and (c) prevention of activation of the complement system are three important items for ensuring biocompatibility. In particular, when the medical device is used as a material that comes in contact with blood for a relatively short time, such as an extracorporeal circulation medical device (for example, artificial kidney or films for plasma skimming), it is generally important to prevent the activation of platelets or the complement system, i.e., the items (b) and (c) above, because an anticoagulant, such as heparin or sodium citrate, is used with the device.

Generally, a microphase-separated surface, a hydrophilic surface, in particular, a gelled surface to which a water-soluble polymer is bonded, are considered superior in (b) prevention of adhesion/activation of platelets, while a hydrophobic surface such as polypropylene is inferior (see Non-Patent Documents 1 and 2). A surface with a microphase-separated structure can exhibit desirable blood compatibility by being rendered into an appropriate phase separation state; however, since the condition for imparting appropriate phase separation is limited, it results in restrictions in use. Further, although adhesion of platelets is suppressed in the gelled surface to which a water-soluble polymer is bonded, problematic irregular variation in blood cell components (platelets) is often observed because of restoration of platelets or microthrombus activated on the material surface.

On the other hand, regarding (c) prevention of activation of the complement system, it is known that a surface having a hydroxy group such as cellulose or ethylene-vinyl alcohol copolymer has high activity, while a hydrophobic surface such as polypropylene has slight activity (see Non-Patent Document 3). Therefore, for example, when a cellulose-based material or a vinyl alcohol-based material is used for a medical tube, it will cause the activation of the complement system; however, if a hydrophobic surface such as polypropylene is used, it will cause the adhesion/activation of platelets.

Further, a medical device that comes in contact with living tissues or body fluid in addition to blood, such as a film for preventing adhesion or an implant material that is implanted into a living body for a long time, or a wound dressing material that comes in contact with a wound area (a wound area with peeling skin and a living body tissue exposed to the surface), is required to have a surface that is not acutely recognized as a foreign substance by a living body, and that must be easily removable from the living body (i.e., they must have non-adhesive surfaces). However, the adhesion of living body tissues to the surface occurs in medical devices composed of polyurethane or polytetrafluoroethylene, which have heretofore been used as the aforementioned medical materials. As a result, these materials are acutely recognized as foreign substances by a living body. For this reason, the performance of these materials has been considered insufficient. Further, although silicone is another material that ensures high biocompatibility, its particularly high detachability hinders secure adhesion to the base material. Thus, it has been difficult to adopt silicone to composite materials and the like.

Polyethyleneglycol (PEG) is another example of a medical material. PEG has significantly superior blood compatibility and has been actively studied to be applied to medical tools. However, because PEG is water-soluble, when PEG is used as a medical material, it is necessary to process PEG into a block copolymer or a graft copolymer with other polymers, thereby fixing it to the surface.

In addition, a known technique is to coat a blood-contact surface of a medical device with poly(2-methoxyethylacrylate), which is a biocompatible material, to render the surface antithrombogenic (see Patent Document 3). However, since this method uses methanol as a solvent for coating, there is a problem of toxic residual methanol.

Further, also known is the use of a water-soluble copolymer of polyethyleneglycol acrylate and acrylic acrylate upon immunoassay analysis for the protection of the solid-phase surface (see Patent Document 4). However, because this copolymer is water-soluble, the biocompatibility will not last long.

Furthermore, a known technique is to impart both desirable biocompatibility and water insolubility by copolymerizing a hydrophilic (meth)acrylate monomer containing a phosphorylcholine group having high biocompatibility, and a alkyl (meth)acrylate monomer having high hydrophobicity (see Patent Document 5). However, since this copolymer has the form of a rigid solid at room temperature, the coating film of this copolymer may peel off; moreover, the biocompatibility in terms of immunity of the copolymer is insufficient.

The applicant of the present invention has already suggested a water-insoluble (meth)acrylate copolymer that is applicable to the blood-contact surface of a medical device and expresses antithrombogenicity for a long period of time (Patent Documents 6 to 9). These documents disclose an antithrombogenic material composed of a copolymer containing polyethyleneglycol(meth)acrylate, which is a hydrophobic monomer, and alkyl (meth)acrylate, which is a hydrophilic monomer. However, these documents nowhere disclose the problems at the coating step inside a polyvinyl chloride medical tube containing a plasticizer, or a means for solving the problems.

Further, Patent Document 10 discloses an antithrombogenic material, which is a (meth)acrylate copolymer composed of hydrophobic (meth)acrylate and hydrophilic (meth) acrylate. This antithrombogenic material contains silicone (meth)acrylate and/or alkyl (meth)acrylate as hydrophobic (meth)acrylate. Further, Patent Document 10 discloses that it is preferable to use methanol, ethanol, or isopropyl alcohol as an organic solvent to be used for the coating of a medical device with the antithrombogenic material. However, use of these alcohols as a coating solvent may cause a problem of plasticizer elution from the polyvinyl chloride medical tube.

Further, Patent Document 11 discloses a technique using an antithrombogenic material containing, as an essential component, an ionic complex of organic cation and heparin (derivative). The antithrombogenic material is dissolved in tetrahydrofuran (THF), and the resulting coating solution is applied to coat the inner cavity of a polyvinyl chloride tube. Since this technique uses THF as a coating solvent, there is a concern of possible elution of a large amount of plasticizer.

CITATION LIST

Patent Document

[Patent Document 1] Japanese Unexamined Patent Application Publication No. 2002-282356
[Patent Document 2] Specification of U.S. Pat. No. 4,627,844
[Patent Document 3] Japanese Unexamined Patent Application Publication No. 2002-105136
[Patent Document 4] Japanese Unexamined Patent Application Publication No. 11-287802
[Patent Document 5] Japanese Unexamined Patent Application Publication No. 11-35605
[Patent Document 6] Japanese Unexamined Patent Application Publication No. 2007-146133
[Patent Document 7] Japanese Unexamined Patent Application Publication No. 2007-197686
[Patent Document 8] Japanese Unexamined Patent Application Publication No. 2008-264266
[Patent Document 9] Japanese Unexamined Patent Application Publication No. 2008-264719
[Patent Document 10] Japanese Unexamined Patent Application Publication No. 2008-289864
[Patent Document 11] Japanese Unexamined Patent Application Publication No. 11-164882

Non-Patent Document

[Non-Patent Document 1] Transactions—American Society for Artificial Internal Organs, vol. XXXIII, pp. 75 to 84 (1987)
[Non-Patent Document 2] Kobunshi to Iryo (Polymer and Medical Treatment, Mita Shuppan-kai, p. 73 (1989)
[Non-Patent Document 3] Artificial Organs 16(2), pp. 1045 to 1050 (1987)

SUMMARY OF INVENTION

Technical Problem

The present invention was made in view of the current circumstances of the aforementioned hitherto-known technologies. An object of the present invention is to provide an easy technique for evenly and efficiently coating the inside of a polyvinyl chloride medical tube containing a plasticizer with a sufficient amount of an antithrombogenic material composed of a specific (meth)acrylate copolymer without causing deterioration in appearance or uneven coating due to elution of the plasticizer.

Solution to Problem

The inventors of the present invention conducted extensive research to attain the aforementioned object and found a method to perform easy and even coating of an antithrombogenic material without the influence of the plasticizer. The method is performed by preparing a solvent composed of water and an alcohol that is adjusted to dissolve the copolymer of the antithrombogenic material but does not dissolve the plasticizer used for polyvinyl chloride, dissolving an antithrombogenic material in the solvent, passing the resulting solution through a tube, thereby coating the inner surface of the tube with the antithrombogenic material without causing elution of the plasticizer inside the tube, then subsequently passing water through the tube so as to unify the film thickness of the antithrombogenic material coating, and finally drying the moisture remaining inside the tube. With this finding, the inventors completed the present invention.

Specifically, the present invention has the following items (1) to (9).

(1) A method for coating an inner surface of a polyvinyl chloride medical tube containing a plasticizer with an antithrombogenic material composed of a copolymer comprising methoxypolyethyleneglycol(meth)acrylate, alkyl (meth)acrylate, and silicone(meth)acrylate, the method comprising the successive steps of:

passing a solution obtained by dissolving an antithrombogenic material in a solvent comprising water and at least one kind of alcohol that dissolves the copolymer but does not dissolve the plasticizer through the inner surface of the tube;

passing water through the tube; and drying the tube.

(2) The method according to (1), wherein the alcohol is selected from the group consisting of methanol, ethanol, 1-propanol, and 2-propanol.

(3) The method according to (2), wherein the solvent comprises water, ethanol, and 1-propanol in a volume ratio of 10 to 30:20 to 40:30 to 60.

(4) The method according to any one of (1) to (3), wherein the copolymer in the solution has a concentration of 0.01 to 10 weight %.

(5) The method according to any one of (1) to (4), wherein the amount of the solution to be passed through the inner surface of the tube is 1 to 20% based on the gross volume of the internal cavity of the tube, and the amount of the water to be passed through the inner surface of the tube is 50 to 300% based on the gross volume of the internal cavity of the tube.

(6) The method according to any one of (1) to (5), wherein the solution and the water are passed through the inner surface of the tube by way of decompression suction.

(7) The method according to any one of (1) to (6), wherein the amount of the antithrombogenic material coating the inner surface of the tube is 1 to 500 μg/cm$^2$.

(8) A medical tube having an inner surface coated with an antithrombogenic material by the method of any one of (1) to (7).

(9) The medical tube according to (8), wherein the inner surface of the tube is coated with 1 to 500 μg of an antithrombogenic material per surface area of 1 cm$^2$.

Advantageous Effects of Invention

The method of the present invention ensures prevention of deterioration in appearance due to elution of a plasticizer contained in the tube, because the method performs the coating of the inner surface of the tube with an antithrombogenic material by using a solvent that dissolves an antithrombogenic material but does not dissolve the plasticizer. Further, the method includes a step of passing water through the tube after the coating with the antithrombogenic material. Therefore, even in the processing of a long tube, the method prevents dripping and shifting of the solution by the force of gravity, thereby enabling even coating with a sufficient amount of an antithrombogenic material.

DESCRIPTION OF EMBODIMENTS

Figure 1:
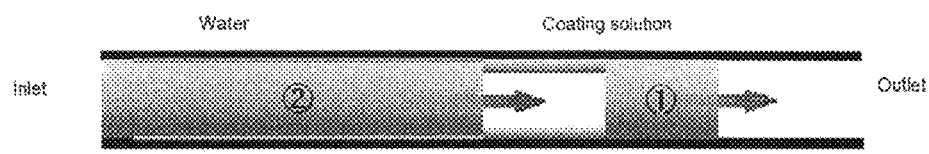
FIG. 1 A pattern diagram of a coating solution and water passing through inside the tube during the method of the present invention.

The present invention is more specifically described below. However, the present invention is not limited to these embodiments.

The method of the present invention is a method for coating the inside of a polyvinyl chloride medical tube with a specific antithrombogenic material. The method is characterized by passing a solution obtained by dissolving an antithrombogenic material in a specific solvent through the tube, subsequently passing water through the tube, and then drying the tube.

The antithrombogenic material used in the method of the present invention is composed of a copolymer containing methoxypolyethyleneglycol(meth)acrylate, alkyl (meth)acrylate, and silicone(meth)acrylate. Each acrylate component is conducive to antithrombogenicity. The ratio (mol %) of these acrylates may be suitably selected from the range of 10 to 80:10 to 80:0.1 to 20, more preferably 20 to 70:20 to 80:0.5 to 10.

Methoxypolyethyleneglycol(meth)acrylate, represented by the General Formula [I] below, has a polyethyleneglycol chain forming a superior hydrophilic surface. By incorporating this monomer into the copolymer, a hydrophilic surface is provided, which serves to prevent protein adsorption or platelet adhesion. However, since such a surface having superior hydrophilicity may also induce elution into the blood, it is necessary to incorporate a hydrophobic monomer into the copolymer to adjust the solubility so as to suppress the elution. It is preferable to use methoxypolyethyleneglycol(meth)acrylate having 2 to 500, more preferably 2 to 100, further preferably 2 to 50, even further preferably 2 to 10 polyethyleneglycol repeating units. More specifically, methoxydiethyleneglycol(meth)acrylate, methoxytriethyleneglycol(meth)acrylate, methoxytetraethyleneglycol(meth)acrylate, methoxypentaethyleneglycol(meth)acrylate, methoxyhexaethyleneglycol(meth)acrylate, methoxyheptaethyleneglycol(meth)acrylate, methoxyoctaethyleneglycol(meth)acrylate, methoxynonaethylene glycol(meth)acrylate, and methoxydecaethyleneglycol(meth)acrylate may be used. If the number of the repeating unit is large and the hydrophilicity excessively increases, the solubility in the blood increases even after the copolymerization, and polyethyleneglycol may be dissolved from the medical material. Therefore, methoxytetraethyleneglycol(meth)acrylate having 4 polyethyleneglycol repeating units and methoxytriethyleneglycol(meth)acrylate having 3 polyethyleneglycol repeating units are particularly preferable.

[Chem. 1]

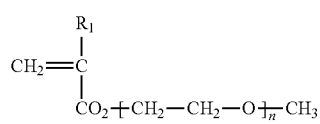

wherein $R_1$ represents a hydrogen atom or a methyl group, and n is an integer 2 to 100.

Further, alkyl (meth)acrylate is represented by General Formula [II] below and contains an alkyl group having hydrophobicity that is conducive to increasing adhesion with a plastic base material, such as polyethylene or polyvinyl chloride. By incorporating this monomer into a copolymer, it is possible to render the copolymer hydrophobic, thereby reducing elution into the blood and improving adhesion with medical base materials. Examples of alkyl (meth)acrylate include normal hexyl (meth)acrylate, cyclohexyl (meth)acrylate, heptyl (meth)acrylate, octyl (meth)acrylate, 2-ethylhexyl (meth)acrylate, nonyl (meth)acrylate, decyl (meth)acrylate, lauryl (meth)acrylate, myristyl (meth)acrylate, palmityl (meth)acrylate, and stearyl (meth)acrylate.

[Chem. 2]

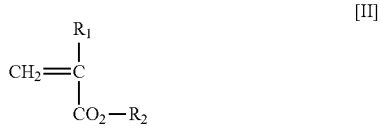

[II]

wherein $R_2$ represents an alkyl or aralkyl group having 2 to 30 carbon atoms, and $R_3$ represents a hydrogen atom or a methyl group.

Further, silicone(meth)acrylate is represented by General Formula [III] below. The incorporation of this monomer provides biocompatibility, i.e., the physiological inertness of silicone, thereby suppressing activation of components in the blood, in particular, activation of complements involved in the immune system. Further, the copolymer contains polydimethylsiloxane as a component. Because polydimethylsiloxane is hydrophobic and has a chain-like form as with polyethyleneglycol, each polydimethylsiloxane forms a hydrophilic segment and a hydrophobic segment, and so the surface energy gap is minimized upon contact with blood. Therefore, each polydimethylsiloxane forms a complicated structure, such as a microphase-separated structure or a fluid mosaic structure, thereby imparting a superior antithrombogenicity. The amount of this monomer is preferably not more than 20 mol % based on the amount of the copolymer. If the amount of the monomer exceeds 20 mol %, defects such as a decrease in solubility in alcohol or a decrease in adhesion with respect to plastic base materials may occur. There is a commercially available silicone(meth)acrylate having 2 to 100 repeating units at the polydimethylsiloxane moiety. In the present invention, if the polydimethylsiloxane repeating unit is too large, the viscosity of the resulting copolymer becomes too high and may result in difficulty in handling. On the other hand, if the polydimethylsiloxane repeating unit is too small, the viscosity excessively decreases and may easily disappear from the application surface of the medical device, etc. Accordingly, it is more preferable that the monomer have 2 to 50, further preferably 5 to 50, even further preferably 10 to 40 polydimethylsiloxane repeating units.

[Chem. 3]

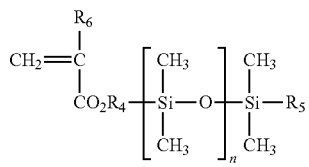

[III]

wherein, $R_4$ represents —$C_3H_6$— or —$C_4H_8$—, $R_5$ represents a $C_{1-6}$ alkyl group, $R_6$ represents a hydrogen atom or a methyl group, and n represents an integer 2 to 100.

The medical tube used in the method of the present invention contains polyvinyl chloride as a major component, and a large amount of plasticizer to ensure flexibility and transparency. Generally, the amount of the plasticizer is 10 to 70 weight % based on the weight of the tube. Conventionally, butyl benzyl phthalate, diethylhexyl phthalate (DEHP), diisodecyl phthalate, diisononyl phthalate, dihexyl phthalate, dioctyl phthalate, and the like are used as a plasticizer. Of these, diethylhexyl phthalate (DEHP) is most frequently used. Further, in recent years, because of concern about plasticizer elution, tris(2-ethylhexyl)trimellitate (TOTM) having a low solubility is used in some cases.

Further, because the aforementioned medical tube is used as a blood circuit of an artificial lung, a blood filter, a centrifugal pump and the like, the medical tube must be connected to these medical devices. Therefore, medical tubes have a specified size; the internal diameter is specified as, for example, ⅛ inch (3.20 mm), ¼ inch (6.40 mm), ⅜ inch (9.53 mm), ½ inch (12.70 mm), and the like. The tube length is adjusted by cutting the tube to a length sufficient for the connection of blood circuit; therefore, the produced tube preferably has a length such as 50 m or 100 m when stored.

In the present invention, the inside of a medical tube is coated with an antithrombogenic material by using a solution in which the antithrombogenic material is dissolved in a specific solvent. Because the tube contains a large amount of plasticizer, it is important to select a solvent capable of evenly coating the tube with the antithrombogenic material without causing elution of the plasticizer from the tube.

When the solvent is selected, it is most important to select one in which the copolymer for constituting the antithrombogenic material is soluble. To ensure even and smooth coating of the copolymer, the copolymer must be dissolved in a solvent. Moreover, to sufficiently exhibit antithrombogenicity, it is necessary to ensure a certain coating amount and a certain film thickness. Other technologies often use a solution in which the copolymer is evenly dispersed without being dissolved, obtained by mixing water and an organic solvent and adding a dispersing agent. Such a solution is called "dispersion" or "emulsion". However, because of the large size of the aggregates of the molecules, this solution has defects including excessively high water content, significantly low wettability of the base material, etc., and thus the coating amount and the film thickness are insufficient in the coating using this solution.

The second important thing is to select a solvent in which the plasticizer contained in the medical tube is insoluble, so as to minimize the elution of the plasticizer. If the plasticizer is eluted from the tube when the tube is coated with the copolymer, it results in a defective appearance. Moreover, it may also cause continuous elution of the plasticizer as the solvent passes through the long tube, in which case, the back portion of the tube may be coated with a mixture of the copolymer and the plasticizer.

The third important thing is to select an appropriate solvent, more specifically, to select a solvent that ensures safety in handling and in medical use. For example, it is preferable to select a solvent from water and various alcohols such as methanol, ethanol, 1-propanol, or 2-propanol. Other solvents are not preferable in terms of safety in handling and toxicity of the residual solvent.

Based on these requirements, the present invention uses a solvent that dissolves the copolymer but does not dissolve the plasticizer, and that is selected from various mixtures of water and at least one kind of alcohol. The selection of the solvent may be based on generally known solubility parameters; however, the solubility parameters are supposed to be used only for reference regarding solubility. Moreover, because the copolymer and the plasticizer have similar solubility parameters, it is not easy to select a solvent satisfying the above conditions.

Therefore, a method for finding the optimum formulation of water and alcohol is described below. This method is based on actual observation of solubilities of plasticizers and copolymers in various solvents.

First, the solubilities of a plasticizer and a copolymer were observed using five solvents, each solely containing water or one of four kinds of alcohol. The confirmation is performed by placing 20 ml of water or one of four kinds of alcohol in a 25-ml beaker, and 1 g of a plasticizer (DEHP, TOTM) is added thereto dropwise. The mixture is stirred with a stirrer for an hour. The mixture in which the plasticizer and the copolymer are completely dissolved is labeled as "○", and the mixture in which an insoluble component was observed is labeled as "x". Further, a copolymer containing methoxytriethyleneglycol acrylate, alkyl acrylate (2-ethylhexyl), and silicone methacrylate (repeating unit in the polydimethylsiloxane moiety: 10) in a molar percent ratio of 35:60:5 is prepared, 20 ml of water or one of four kinds of alcohol is placed in a 25-ml beaker, and then 1 g of the copolymer is placed in the beaker. The mixture is stirred with a stirrer for an hour. The mixture in which the plasticizer and the copolymer are completely dissolved is labeled as "○", and the mixture in which an insoluble component is observed is labeled as "x". Table 1 shows the result of solubilities of DEHP (diethylhexyl phthalate) and TOTM (tris(2-ethylhexyl)trimellitate) as plasticizers, and the solubility of the copolymer constituting the antithrombogenic material in water or one of four kinds of alcohol. As shown in Table 1, none of the solvents each containing water or four kinds of alcohol were confirmed as a solvent that dissolves a copolymer but does not dissolve a plasticizer (DEHP, TOTM).

TABLE 1

|  | Water | Methanol | Ethanol | 1-Propanol | 2-Propanol |
|---|---|---|---|---|---|
| DEHP | x | ○ | ○ | ○ | ○ |
| TOTM | x | ○ | ○ | ○ | ○ |
| Polymer | x | x | ○ | ○ | ○ |

Insoluble = x
Soluble = ○

Next, the solubilities of the plasticizer and the copolymer in mixed solvents of water and one of the four alcohols were confirmed. Table 2 shows the results of visual inspection for the presence/absence of insoluble components in mixed solvents of water and one of the four alcohols. The inspection was performed by first dissolving 0.1 g of either a plasticizer (DEHP) or a copolymer constituting an antithrombogenic material in 1 ml of each alcohol, and then adding thereto water multiple times in an amount of 0.1 ml each time. As shown in Table 2, none of the mixed solvents each containing water and one of the four kinds of alcohol were confirmed as a solvent that dissolves a copolymer but does not dissolve a plasticizer (DEHP).

TABLE 2

Solutility of DEHP

| Amount of Water (ml) | Solvent (1 ml) | | | |
|---|---|---|---|---|
|  | Methanol | Ethanol | 1-Propanol | 2-Propanol |
| 0 | ○ | ○ | ○ | ○ |
| 0.1 | X | ○ | ○ | ○ |
| 0.2 | X | X | ○ | ○ |
| 0.3 | X | X | ○ | ○ |
| 0.4 | X | X | ○ | X |
| 0.5 | X | X | ○ | X |
| 0.6 | X | X | X | X |

Solubility of Copolymer

| Amount of Water (ml) | Solvent (1 ml) | | | |
|---|---|---|---|---|
|  | Methanol | Ethanol | 1-Propanol | 2-Propanol |
| 0 | X | ○ | ○ | ○ |
| 0.1 | X | ○ | ○ | ○ |
| 0.2 | X | X | ○ | ○ |
| 0.3 | X | X | ○ | ○ |
| 0.4 | X | X | ○ | X |
| 0.5 | X | X | ○ | X |
| 0.6 | X | X | X | X |

X Insoluble component was observed
○ Insoluble component was not observed

Table 3 shows the results of visual inspection with respect to mixed solvents of water and one of the four alcohols, using TOTM as a plasticizer instead of DEHP. As shown in Table 3, there was one case in which the plasticizer (TOTM) was not dissolved but the copolymer was dissolved among mixed solvents of water and 1-propanol (see the encircled part in Table 3).

TABLE 3

Solutility of TOTM

| Amount of Water (ml) | Solvent (1 ml) | | | |
|---|---|---|---|---|
|  | Methanol | Ethanol | 1-Propanol | 2-Propanol |
| 0 | ○ | ○ | ○ | ○ |
| 0.1 | X | ○ | ○ | ○ |
| 0.2 | X | X | ○ | ○ |
| 0.3 | X | X | ○ | ○ |
| 0.4 | X | X | ○ | X |
| 0.5 | X | X | X | X |
| 0.6 | X | X | X | X |

TABLE 3-continued

Solubility of Copolymer

| Amount of Water (ml) | Solvent (1 ml) | | | |
|---|---|---|---|---|
| | Methanol | Ethanol | 1-Propanol | 2-Propanol |
| 0 | X | O | O | O |
| 0.1 | X | O | O | O |
| 0.2 | X | X | O | O |
| 0.3 | X | X | O | O |
| 0.4 | X | X | O | X |
| 0.5 | X | X | O | X |
| 0.6 | X | X | X | X |

X Insoluble component was observed
O Insoluble component was not observed

Next, the solubilities of the plasticizer and the copolymer in mixed solvents of water and two (ethanol and 1-propanol) of the four alcohols were confirmed. Table 3 shows the results of visual inspection for the presence/absence of insoluble components in mixed solvents of water and the two alcohols. The inspection was performed by first dissolving 0.1 g of either a plasticizer (DEHP) or a copolymer constituting an antithrombogenic material in 1 ml of a mixture of ethanol and 1-propanol, and then adding thereto water plural times in an amount of 0.1 ml each time. The proportion of ethanol and 1-propanol in the mixture was varied from 10:0 to 0:10 by weight. As shown in Table 4, there were some cases in which the plasticizer (DEHP) was not dissolved but the copolymer was dissolved among mixed solvents of water, ethanol, and 1-propanol (see the cells showing crosses in the table on the left and showing circles in the table on the right in the areas shown by the solid line in Table 4).

TABLE 4

Solutility of DEHP

| Amount of Water (ml) | Solvent (1 ml) Ratio of Ethanol:1-Propanol (Upper Row:Lower Row) | | | | | | | | | | |
|---|---|---|---|---|---|---|---|---|---|---|---|
| | 10 | 9 | 8 | 7 | 6 | 5 | 4 | 3 | 2 | 1 | 0 |
| | 0 | 1 | 2 | 3 | 4 | 5 | 6 | 7 | 8 | 9 | 10 |
| 0 | O | O | O | O | O | O | O | O | O | O | O |
| 0.1 | O | O | O | O | O | O | O | O | O | O | O |
| 0.2 | X | X | O | O | O | O | O | O | O | O | O |
| 0.3 | X | X | X | X | X | O | O | O | O | O | O |
| 0.4 | X | X | X | X | X | X | X | X | X | O | O |
| 0.5 | X | X | X | X | X | X | X | X | X | X | O |
| 0.6 | X | X | X | X | X | X | X | X | X | X | X |

Solubility of Copolymer

| Amount of Water (ml) | Solvent (1 ml) Weight Ratio of Ethanol:1-Propanol | | | | | | | | | | |
|---|---|---|---|---|---|---|---|---|---|---|---|
| | 10 | 9 | 8 | 7 | 6 | 5 | 4 | 3 | 2 | 1 | 0 |
| | 0 | 1 | 2 | 3 | 4 | 5 | 6 | 7 | 8 | 9 | 10 |
| 0 | O | O | O | O | O | O | O | O | O | O | O |
| 0.1 | O | O | O | O | O | O | O | O | O | O | O |
| 0.2 | X | X | O | O | O | O | O | O | O | O | O |
| 0.3 | X | X | X | X | O | O | O | O | O | O | O |
| 0.4 | X | X | X | X | X | X | O | O | O | O | O |
| 0.5 | X | X | X | X | X | X | X | X | O | O | O |
| 0.6 | X | X | X | X | X | X | X | X | X | O | X |

X Insoluble component was observed
O Insoluble component was not observed

Table 5 shows the results of visual inspection with respect to mixed solvents of water and two alcohols (ethanol and 1-propanol), using TOTM as a plasticizer instead of DEHP. As shown in Table 5, there were some cases in which the plasticizer (TOTM) was not dissolved but the copolymer was dissolved among mixed solvents of water, ethanol, and 1-propanol (see the cells showing crosses in the table on the left and showing circles in the table on the right in the areas shown by the solid line in Table 5).

TABLE 5

Solubility of TOTM

| Amount of Water (ml) | Solvent Weight Ratio of Ethanol:1-Propanol | | | | | | | | | | |
|---|---|---|---|---|---|---|---|---|---|---|---|
| | 10 | 9 | 8 | 7 | 6 | 5 | 4 | 3 | 2 | 1 | 0 |
| | 0 | 1 | 2 | 3 | 4 | 5 | 6 | 7 | 8 | 9 | 10 |
| 0 | O | O | O | O | O | O | O | O | O | O | O |
| 0.1 | O | O | O | O | O | O | O | O | O | O | O |
| 0.2 | X | X | X | O | O | O | O | O | O | O | O |
| 0.3 | X | X | X | X | X | X | X | O | O | O | O |
| 0.4 | X | X | X | X | X | X | X | X | X | O | O |
| 0.5 | X | X | X | X | X | X | X | X | X | X | X |
| 0.6 | X | X | X | X | X | X | X | X | X | X | X |

Solubility of Copolymer

| Amount of Water (ml) | Solvent Weight Ratio of Ethanol:1-Propanol | | | | | | | | | | |
|---|---|---|---|---|---|---|---|---|---|---|---|
| | 10 | 9 | 8 | 7 | 6 | 5 | 4 | 3 | 2 | 1 | 0 |
| | 0 | 1 | 2 | 3 | 4 | 5 | 6 | 7 | 8 | 9 | 10 |
| 0 | O | O | O | O | O | O | O | O | O | O | O |
| 0.1 | O | O | O | O | O | O | O | O | O | O | O |
| 0.2 | X | X | X | O | O | O | O | O | O | O | O |
| 0.3 | X | X | X | X | O | O | O | O | O | O | O |
| 0.4 | X | X | X | X | X | X | O | O | O | O | O |
| 0.5 | X | X | X | X | X | X | X | X | O | O | O |
| 0.6 | X | X | X | X | X | X | X | X | X | O | X |

The above method may also adopt various other mixed solvents of water and alcohols, and other plasticizers. Further, by adopting more solvents with even more minute adjustment of the alcohol formulation and proportion or water amount according to the obtained results, it is possible to precisely understand the exact range of the optimum solvent formulation. The solvent used in the present invention contains water, ethanol, and 1-propanol preferably in a volume ratio of 5 to 40:0 to 50:20 to 80, more preferably 5 to 35:15 to 45:25 to 65. It is thought that the reason why the solvent in which the plasticizer was not dissolved but the copolymer was dissolved was found among the mixed solvents of water and at least one kind of alcohol is that because the copolymer is composed of a hydrophilic component (polar component) and a hydrophobic component (nonpolar component), the mixture of the polar component (water) and the nonpolar component (alcohol) in the solvent increases the solubility of the copolymer. Further, because the plasticizer is composed of a single molecule, there is no significant change in solubility of the plasticizer in the mixed solvents of polar components and nonpolar components.

Next, a solution was obtained by dissolving an antithrombogenic material in the solvent of water and at least one kind of alcohol prepared as above. Here, the content of the antithrombogenic material in the solution is preferably 0.01 to 10 weight %. If the content of the antithrombogenic material falls below this range, it is not possible to coat the tube surface with a sufficient amount of the antithrombogenic material. If the content of the antithrombogenic material exceeds this range, the amount and the thickness of the coating become excessive, thereby making the inner surface of the tube sticky. Such stickiness may cause defects in connecting to or detaching from other base materials.

In the method of the present invention, as described above, first, the resulting solution is supplied into the tube to be passed therethrough as a coating solution, and then water (preferably distilled water) is supplied thereto to be passed therethrough, and then the tube is dried. FIG. 1 shows a pattern diagram of the coating solution and water passing through the tube. As shown in FIG. 1, the coating solution first comes in contact with the inner surface of the tube, and as a result, the antithrombogenic material is adsorbed to the inner surface of the tube. Thereafter, as water subsequently supplied thereto passes through the tube, the extra coating solution is pushed to the outlet. The coating of the inner surface of the tube with the antithrombogenic material is completed at this point. The small amount of residual water inside the tube can be simply removed by drying.

A preferable amount of the coating solution is 1 to 20% based on the gross volume of the internal cavity of the tube. It is necessary that the amount of the coating solution be at least 1% because the coating solution must be evenly supplied to the inner surface of the tube. More specifically, the amount of the coating solution gradually decreases during the supply of the coating solution into the tube, because the coating solution adheres to the inner surface of the tube. Therefore, it is necessary to ensure a certain amount of the coating solution. For example, in the coating of a 100-m tube, the amount of the coating solution that passes through the tube is equal to 1 m of the tube, which is a minimum required amount for ensuring proper coating. There is no upper limit to the amount of the coating solution; however, the amount is preferably not more than 20% in terms of the costs of the material and the time consumed. On the other hand, the amount of water to be subsequently supplied is preferably 50 to 300% based on the gross volume of the internal cavity of the tube. If the amount of water falls below 50%, the coating solution cannot be sufficiently washed off, thereby making the coating uneven. It is not preferable that the amount of water exceeds 300% in terms of the costs of the material and the time consumed.

The method for supplying the coating solution and water to allow them to pass through the tube is preferably performed by decompression suction using a vacuum pump or the like. It is also possible to supply the coating solution and water under increased pressure; however, in this method, a huge pressure is applied to the connecting inlet of the tube, thus causing operating risks including breakage or deformation of the tube, or detachment of the tube, which results in spreading the solution. Further, the method under increased pressure may cause sagging of the coating solution under atmospheric pressure. As a result, the coating solution may not be in contact with the entire part of the inner surface of the tube.

Figure 2:
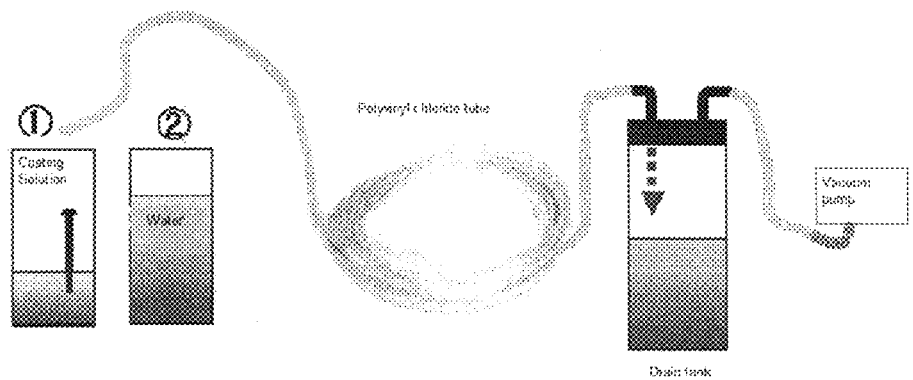
FIG. 2 A schematic view of an apparatus for coating an inner surface of a tube used in the method of the present invention.

FIG. 2 shows a schematic view of an example of an apparatus for coating an inner surface of a tube used in the actual coating method. One end of the tube is connected to a drain tank connected to a vacuum pump, while a fixed amount of the coating solution is sucked through the other end of the tube so as to be passed through the tube. Subsequently, water is sucked in. This switching of the liquids may be performed by lifting the tube end by hand and transferring the tube end from the container of the coating solution to the container of water, or may otherwise be performed by using an automatic switchover valve.

The timing of switching the liquids is preferably controlled so that a distance of 1 to 100 cm is provided between the coating solution and water in the tube, thereby allowing air to be present therebetween. If the distance is less than 1 cm or if air is not present between the coating solution and water in the tube, the coating solution and water may be mixed during the step of supplying these liquids. Further, if the distance is longer than 100 cm, there is a possibility that the component of the coating solution being supplied and passing through the tube will evaporate before water is supplied, thus changing the compositional ratio of the solvent or making the coating surface uneven. To ensure a distance of 1 cm to 100 cm, it is preferable to switch the liquids at intervals of about 0.5 to 3 seconds if the switching is performed by lifting the tube by hand. Specifically, for example, when a tube having a diameter of ⅜ inch and a length of 100 m is coated, the coating liquid is first sucked in for about 3 seconds using a vacuum pump having a maximum vacuum level of −80 kPa and a discharge air amount of 25 L/minute, and then air is sucked in for about 1 second to make an air layer having a length of 30 cm in the tube. Thereafter, the washing water is sucked in for about 5 minutes.

After water is sucked in, it is necessary to dry the tube so as to remove the residual water inside the tube. The drying is preferably performed, for example, by circulating nitrogen or air at 5 to 40° C., more preferably, at 20 to 30° C., inside the tube. The circulation time varies depending on the tube length. For a tube having a length of about 100 m, drying will be completed by circulating nitrogen at 25° C. for about 4 hours. If heat of more than 40° C. is supplied to the tube for a long time, it causes problems of transfer of printed letters, elution of the plasticizer, degradation of the tube, and the like.

As described above, the method of the present invention supplies a large amount of water into the tube after supplying the coating solution. Therefore, the coating can be completed after the supply of water, thereby significantly simplifying the subsequent drying step. The drying step is performed only to remove water. Because organic solvents are usually used for the solvents for copolymer coating, the drying temperature and drying duration of the organic solvent affect the coating state and quality. Therefore, it is necessary to appropriately set the temperature and duration. To quickly remove an organic solvent so as to ensure even coating of the tube, it is necessary to apply high temperature heat; however, such application of high temperature heat may result in unwanted influence on the tube. The method of the present invention suffers no such problems or difficulties in the drying step.

Figure 3:
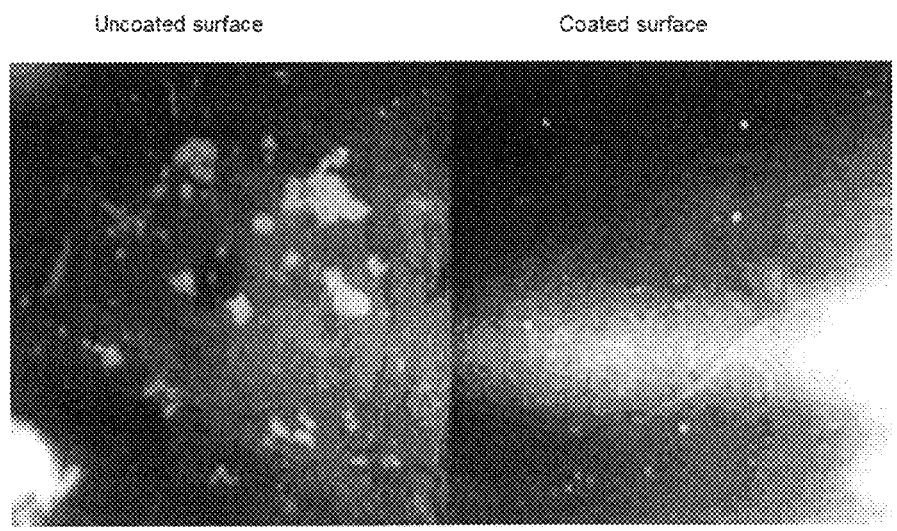
FIG. 3 Microscope images showing platelet adhesion in a coated surface and in an uncoated surface according to the method of the present invention.

The tube completed in coating with the antithrombogenic material by the method of the present invention has no defects such as elution of the plasticizer or uneven coating. The condition of the tube is exactly the same as that before the coating, maintaining a desirable appearance. Moreover, because the inner surface of the tube is evenly coated with a sufficient amount of an antithrombogenic material, the tube exhibits a superior antithrombogenicity. The antithrombogenicity can be confirmed using the capability of inhibiting platelet adhesion as an index. For example, it can be confirmed by performing the following test. An inner tube portion near the outlet is overlaid with another tube having a smaller diameter so that they are in contact with each other, and the overlaid tubes are coated with an antithrombogenic material in the aforementioned method of the present invention. Then, the smaller tube is taken out after the coating to make an uncoated surface (the surface identical to the tube before coating), and the coated surface and the uncoated surface are compared in terms of antithrombogenicity. As evident in the microscope photos in FIG. 3 showing these surfaces, a large amount of platelets is adhered to the uncoated surface, while such adhesion is hardly observed in the coated surface. As such, the tube coated by the method of the present invention exhibits a sufficient antithrombogenicity to the extent that the coating interface is distinct.

Figure 4:
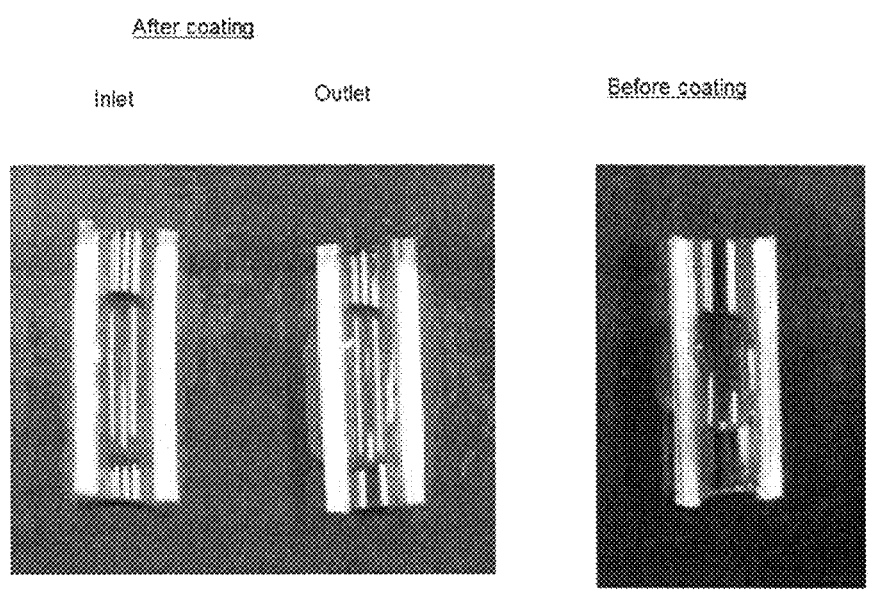
FIG. 4 Photos showing a part of a tube before and after (inlet and outlet) the coating according to the method of the present invention.

Next, the tube obtained by the method of the present invention was subjected to a test to examine for the existence of uneven coating. Since the tube coated with an antithrombogenic material has improved hydrophilicity compared with an uncoated tube, the existence of uneven coating can be confirmed by comparing the hydrophilicities of the inlet and outlet of the coated tube. The hydrophilicities were confirmed by adding 0.5 ml of water dropwise to each of the 5-cm tube pieces taken from the inlet and outlet of a coated 100-m tube. As shown in the photos of an uncoated tube piece and coated tube pieces (inlet and outlet) in FIG. 4, the coated tube pieces have superior hydrophilicity, making the dropped water spread vertically on the tube. The extent of the spread is substantially the same in the inlet and the outlet. As such, the method of the present invention makes it possible to evenly coat the entire length of a tube with an antithrombogenic material.

The amount of the antithrombogenic material to be used to coat the inner surface of the tube in the method of the present invention is preferably 1 to 500 μg/cm². If the amount of the antithrombogenic material falls below 1 μg/cm², it is not possible to coat the entire inner surface of the tube with the antithrombogenic material. In this case, antithrombogenicity may not be sufficiently exhibited. Further, if the amount of the antithrombogenic material exceeds 500 μg/cm², it imparts a lubricating property to the inner surface of the tube. In this case, the tensile strength of the tube may decrease when the tube is connected to other apparatuses as a blood circuit.

EXAMPLES

Excellent effects of the method of the present invention are shown in the following Examples; however, the present invention is not limited to these Examples. The evaluation in the Examples was performed according to the method described below.

(1) Solubility of Plasticizer and Antithrombotic Material

After 1 g of a plasticizer or antithrombotic material was added to 10 ml of a solvent, the container was sealed and shaken using a shaker for 6 hours. Thereafter, the container was allowed to stand for 24 hours, and visual observation was made for the presence of white turbidity or precipitates. The presence of white turbidity or precipitates was described as "x", meaning no solubility, and the absence of white turbidity or precipitates was described as "○", meaning with solubility.

(2) Amount of Antithrombotic Material on Tube Inside Surface

A tube was cut near the center so that the tube inside surface had an area of 100 cm². The antithrombotic material on the cut tube inside surface was extracted with 50 ml of ethanol, and drying and hardening were performed under reduced pressure (about 50° C.). 5 ml of THF was added to the residue and the residue was dissolved in the THF to prepare a sample solution. Separately, 50 mg of an antithrombotic material was dissolved in THF to have a concentration of 5 mg/ml, and the undiluted solution was further diluted with THF to prepare a standard solution (100, 200, 500, 1,000, 3,000, or 5,000 μg/ml). The sample solution and the standard solution were measured by a high-speed liquid chromatography (HPLC) method. The calibration curve was prepared by using the standard solution, and the concentration in the sample solution was calculated using the calibration curve. The amount of the antithrombotic material was calculated based on the concentration in the sample solution. HPLC conditions were as follows.

HPLC Conditions
 Analysis Column
TS gel Multipore HXL-M (styrene vinylbenzene copolymer resin organic solvent column), inner diameter: 7.8 mm, length: 300 mm, particle size: 5 μm, produced by Tosoh Corporation.
 Guard Column
TSK guard column MP (XL), inner diameter: 6.0 mm, length: 40 mm, particle size: 5 μm, produced by Tosoh Corporation.
 Mobile Phase
Tetrahydrofuran (THF) for HMLC (no stabilizer).
 Flow Rate
1.0 mL/min
 Column Set Temperature
40° C.
 Detection
UV 220 nm
 Sample Injection Amount
50 μL (3) Appearance Evaluation In a tube in which an antithrombotic material was coated, followed by drying, it was evaluated whether oil-like droplets (oil trace) and white turbidity (white turbidity trace) were able to be visually observed. The results without trace were rated "good", and the results with trace were rated "poor."

(4) Haemocompatibility
 Platelet Adhesion Test

A tube (inner diameter: ⅜ inch) in which an antithrombotic material was coated, followed by drying, and a tube (inner diameter: ⅜ inch) without coating were both cut into pieces 1.5 cm in length and further cut into semicircle shapes to form curved sheets. 0.5 ml of citric acid-added human plasma (supernatant obtained by centrifuging citric acid-added fresh human blood for 20 minutes at 250×g) was added dropwise to each sheet surface, and the sheet was allowed to stand at 37° C. for 4 hours. Thereafter, washing was fully performed with physiological saline, and the sheet was immersed in a 2.5% glutaraldehyde physiological saline solution for 1 hour. Subsequently, washing was fully performed with distilled water for injection, followed by freeze-drying. Each sheet obtained was observed using a scanning electron microscope (SEM, produced by Hitachi Ltd., model: S-4000) at 1000-fold magnification. When the amount of platelets attached to the surface of the coated sheet was less than one-tenth of that of the sheet without coating, the result was rated "good" considering that an excellent platelet adhesion inhibitory effect was exhibited. When the amount of platelets attached to the surface of the coated sheet was one-tenth or more of that of the sheet without coating, the result was rated "poor". When it is obvious whether the amount is less than one-tenth from an SEM photograph, visual judgment is allowed; however, when the judgment is difficult, an enlarged photocopy of an SEM photograph may be prepared, a grid of 50×50 squares was made, and the areas taken up by the white portion (platelet adhesion portion) and the black portion (platelet non-adhesion portion) may be calculated and compared.

Complement Activation Test

A tube (inner diameter: ¼ inch) in which an antithrombotic material was coated, followed by drying, and a tube (inner diameter: ¼ inch) without coating were cut into pieces 1.5 cm in length. 1 ml of human serum (supernatant obtained by centrifuging for 20 minutes at 1500×g fresh human blood that had been allowed to stand for 4 hours at room temperature) was added, and both ends were clamped. These tubes were incubated at 37° C. for 2 hours. 12.5 µl of the obtained liquid inside the tube, 2.6 ml of a diluted solution of Auto CH50 Seiken (produced by Denka Seiken Co., Ltd.), and 0.4 ml of sensitized sheep red blood cells were mixed, and the mixture was incubated at 37° C. for 1 hour. The mixture was then centrifuged for 10 minutes at 670×g to precipitate red blood cells that were not hemolyzed, and the absorbance of the resulting supernatant was measured at a wavelength of 541 nm, considering that the absorbance of distilled water at a wavelength of 541 nm was 0. When the absorbance measured in the coated tube was 1.2 or greater than that of the tube without coating, the result was rated "good" considering that a complement activity inhibitory effect was exhibited. When the absorbance was less than 1.2 times, the result was rated "poor".

Persistence Test

A tube (inner diameter: ⅜ inch) in which an antithrombotic material was coated, followed by drying, and a tube (inner diameter: ⅜ inch) without coating were cut into pieces 1.5 cm in length, and further cut into semicircle shapes to form curved sheets. Each sheet was subjected to aging in 100 ml of water at 37° C. for 7 days and fully dried, and 0.2 ml of water was added dropwise to the sheet surface. When the diameter of the dropwise-added water droplets in the coated sheet was at least 1.2 times higher than that in the sheet without coating, the result was rated "good" considering that the copolymer was left on the surface. When the diameter was less than 1.2 times, the result was rated "poor".

Comprehensive Haemocompatibility Judgment

The results rated "good" when the all three items in the above three tests were rated "⊙", the results rated "good" when two of the three items were rated "○", and the other results were rated "x".

Examples 1 to 10

A polyvinyl chloride tube (100 m in length, containing 60 wt % of plasticizer DEHP) having an inner diameter of 9.53 mm (⅜ inch) was prepared and mounted on the device shown in FIG. 2. On the other hand, an antithrombotic material and a solvent having the composition shown in Table 6 were prepared, and the antithrombotic material was dissolved in the solvent so that the antithrombotic material had a concentration shown in Table 6, thereby obtaining a coating solution. The coating solution was put into container 1 of the device shown in FIG. 2, and distilled water was put into container 2. The vacuum pump (maximum vacuum level: −80 kPa, discharge air amount: 25 L/min) was operated. First, one end of the tube was immersed in container 1 to pass through the coating solution for 3 seconds. Thereafter, air suction was performed for 1 second, and the tube was immersed in container 2 to pass through distilled water for 300 seconds. Subsequently, nitrogen at 25° C. was circulated inside the tube for 4 hours to perform drying, thereby obtaining a tube in which coating was completed. The evaluation results and details of the antithrombotic material, solvent, plasticizer, etc., used in each Example are shown in Table 6.

The production method of the copolymer of the antithrombotic material in Table 6 is shown below.

Copolymers of Examples 1 to 5, Examples 8 to 10, and Comparative Examples 1 to 5

0.41 g of azobisisobutyronitrile (AIBN) (Wako Pure Chemical Industries, Ltd.) was added to a mixture of 157.1 g of methoxytriethyleneglycol acrylate (MTEGA) (Shin-Nakamura Chemical Co., Ltd.), 231.1 g of alkyl (2-ethylhexyl) acrylate (EHA) (Tokyo Kasei Kogyo Co., Ltd.), and 52.4 g of silicone methacrylate (dimethylsiloxane repeating unit: 10, Shin-Etsu Chemical Co., Ltd.) to perform polymerization reaction in 828 g of ethyl acetate (Tokyo Kasei Kogyo Co., Ltd.) at 80° C. for 20 hours. After completion of the polymerization reaction, the reaction mixture was added dropwise to methanol to perform precipitation, and the product was isolated. The operation in which the product was dissolved in tetrahydrofuran (THF) and added dropwise to methanol was performed two times, thereby purifying the product. The resultant was dried at 60° C. under reduced pressure for one full day.

Copolymer of Example 6

0.41 g of azobisisobutyronitrile (AIBN) (Wako Pure Chemical Industries, Ltd.) was added to a mixture of 218.3 g of methoxynonaethyleneglycol acrylate (MNEGA) (Shin-Nakamura Chemical Co., Ltd.), 180.6 g of alkyl (2-ethylhexyl) acrylate (EHA) (Tokyo Kasei Kogyo Co., Ltd.), 20.0 g of silicone methacrylate (dimethylsiloxane repeating unit: 35, Shin-Etsu Chemical Co., Ltd.) to perform polymerization reaction in 828 g of ethyl acetate (Tokyo Kasei Kogyo Co., Ltd.) at 80° C. for 20 hours. After completion of the polymerization reaction, the reaction mixture was added dropwise to methanol to perform precipitation, and the product was isolated. The operation in which the product was dissolved in tetrahydrofuran (THF) and added dropwise to methanol was performed two times, thereby purifying the product. The resultant was dried at 60° C. under reduced pressure for one full day to obtain a copolymer.

Copolymer of Example 7

0.58 g of azobisisobutyronitrile (AIBN) (Wako Pure Chemical Industries, Ltd.) was added to a mixture of 283.7 g of methoxytriethyleneglycol acrylate (MNEGA) (Shin-Nakamura Chemical Co., Ltd.), 92.1 g of alkyl (2-ethylhexyl) acrylate (EHA) (Tokyo Kasei Kogyo Co., Ltd.), and 120.7 g of silicone methacrylate (dimethylsiloxane repeating unit: 10, Shin-Etsu Chemical Co., Ltd.) to perform polymerization reaction in 1151 g of ethyl acetate (Tokyo Kasei Kogyo Co., Ltd.) at 80° C. for 20 hours. After completion of the polymerization reaction, the reaction mixture was added dropwise to methanol to perform precipitation, and the product was isolated. The operation in which the product was dissolved in tetrahydrofuran (THF) and added dropwise to methanol was performed two times, thereby purifying the product. The resultant was dried at 60° C. under reduced pressure for one full day to obtain a copolymer.

Comparative Example 1

A tube in which coating was completed was obtained in the same manner as in Example 1 except that distilled water was not passed through the inside of the tube. The evaluation results and details of antithrombotic material, solvent, plasticizer, etc., used in Comparative Example 1 are shown in Table 6.

Comparative Examples 2 and 3

A tube in which coating was completed was obtained in the same manner as in Example 1 except that a plasticizer-dissolvable and antithrombotic-material-dissolvable solvent composed of water and alcohol, as shown in Table 6, was used. The evaluation results and details of antithrombotic material, solvent, plasticizer, etc., used in Comparative Examples 2 and 3 are shown in Table 6.

Comparative Example 4

A tube in which coating was completed was obtained in the same manner as in Example 1 except that a plasticizer-nondissolvable and antithrombotic-material-nondissolvable solvent composed of water and alcohol, as shown in Table 6, was used. The evaluation results and details of antithrombotic material, solvent, plasticizer, etc., used in Comparative Example 4 are shown in Table 6.

Comparative Example 5

A tube in which coating was completed was obtained in the same manner as in Example 1 except that a plasticizer-dissolvable and antithrombotic-material-dissolvable solvent composed of alcohol, as shown in Table 6, was used. The evaluation results and details of antithrombotic material, solvent, plasticizer, etc., used in Comparative Example 5 are shown in Table 6.

TABLE 6

| | | Example 1 | Example 2 | Example 3 | Example 4 | Example 5 |
|---|---|---|---|---|---|---|
| Composition of antithrombogenic material (mol %) | Methoxypolyethyleneglycol(meth)acrylate | 35 | 35 | 35 | 35 | 35 |
| | Alkyl(meth)acrylate | 60 | 60 | 60 | 60 | 60 |
| | Silicone(meth)acrylate | 5 | 5 | 5 | 5 | 5 |
| Composition of solvent (vol %) | Water | 20 | 20 | 20 | 30 | 10 |
| | Ethanol | 30 | 40 | 20 | 40 | 30 |
| | 1-Propanol | 50 | 40 | 60 | 30 | 60 |
| Concentration of antithrombogenic material (wt %) | | 0.5 | 0.5 | 0.5 | 0.5 | 0.5 |
| Kind of plasticizer | | DEHP | DEHP | DEHP | DEHP | DEHP |
| Solubility of plasticizer | | X | X | X | X | X |
| Solubility of antithrombogenic material | | ○ | ○ | ○ | ○ | ○ |
| Whether water is passed or not | | Passed | Passed | Passed | Passed | Passed |
| Amount of antithrombogenic material on tube inside surface ($\mu g/cm^2$) | | 24.5 | 20.3 | 26.2 | 22.5 | 33.5 |
| Appearance | Oil trace | Good | Good | Good | Good | Good |
| | White turbidity trace | Good | Good | Good | Good | Good |
| Blood compatibility | | ◎ | ◎ | ◎ | ◎ | ◎ |

| | | Example 6 | Example 7 | Example 8 | Example 9 | Example 10 |
|---|---|---|---|---|---|---|
| Composition of antithrombogenic material (mol %) | Methoxypolyethyleneglycol(meth)acrylate | 20 | 65 | 35 | 35 | 35 |
| | Alkyl(meth)acrylate | 79 | 25 | 60 | 60 | 60 |
| | Silicone(meth)acrylate | 1 | 10 | 5 | 5 | 5 |
| Composition of solvent (vol %) | Water | 20 | 20 | 20 | 20 | 20 |
| | Ethanol | 30 | 30 | 0 | 30 | 30 |
| | 1-Propanol | 50 | 50 | 80 | 50 | 50 |
| Concentration of antithrombogenic material (wt %) | | 0.5 | 0.5 | 0.5 | 0.1 | 3.0 |
| Kind of plasticizer | | DEHP | DEHP | DEHP | DEHP | DEHP |
| Solubility of plasticizer | | X | X | X | X | X |
| Solubility of antithrombogenic material | | ○ | ○ | ○ | ○ | ○ |
| Whether water is passed or not | | Passed | Passed | Passed | Passed | Passed |
| Amount of antithrombogenic material on tube inside surface ($\mu g/cm^2$) | | 23.7 | 22.6 | 27.3 | 5.3 | 137.4 |
| Appearance | Oil trace | Good | Good | Good | Good | Good |
| | White turbidity trace | Good | Good | Good | Good | Good |
| Blood compatibility | | ◎ | ◎ | ◎ | ○ | ◎ |

| | | Comp. Ex. 1 | Comp. Ex. 2 | Comp. Ex. 3 | Comp. Ex. 4 | Comp. Ex. 5 |
|---|---|---|---|---|---|---|
| Composition of antithrombogenic material (mol %) | Methoxypolyethyleneglycol(meth)acrylate | 35 | 35 | 35 | 35 | 35 |
| | Alkyl(meth)acrylate | 60 | 60 | 60 | 60 | 60 |
| | Silicone(meth)acrylate | 5 | 5 | 5 | 5 | 5 |
| Composition of solvent (vol %) | Water | 20 | 5 | 10 | 90 | 0 |
| | Ethanol | 30 | 15 | 0 | 10 | 0 |
| | 1-Propanol | 50 | 80 | 90 | 0 | 100 |
| Concentration of antithrombogenic material (wt %) | | 0.5 | 0.5 | 0.5 | 0.5 | 0.5 |
| Kind of plasticizer | | DEHP | DEHP | DEHP | DEHP | DEHP |
| Solubility of plasticizer | | X | ○ | ○ | X | ○ |
| Solubility of antithrombogenic material | | ○ | ○ | ○ | X | ○ |
| Whether water is passed or not | | Not passed | Passed | Passed | Passed | Passed |

TABLE 6-continued

| | | | | | | |
|---|---|---|---|---|---|---|
| Amount of antithrombogenic material on tube inside surface ($\mu g/cm^2$) | | 24.5 | 32.1 | 29.5 | 0.7 | 21.3 |
| Appearance | Oil trace | Good | Poor | Poor | Good | Poor |
| | White turbidity trace | Poor | Good | Good | Poor | Good |
| Blood compatibility | | ○ | ○ | ○ | X | ○ |

Examples 1' to 10' and Comparative Examples 1' to 5'

Tubes in which coating was completed were obtained in the same manner as in Examples 1 to 10 and Comparative Examples 1 to 5, except that the plasticizer was changed from DEHP to TOTM. The tubes obtained in Examples 1' to 10' and Comparative Examples 1' to 5' had the same evaluation results as the tubes obtained in Examples 1 to 10 and Comparative Examples 1 to 5.

INDUSTRIAL APPLICABILITY

According to the method of the present invention, an inner surface of a tube can be uniformly and efficiently coated with a sufficient amount of an antithrombogenic material without causing deterioration in appearance or uneven coating due to elution of the plasticizer; therefore, the method of the present invention is extremely useful in producing medical tubes connected to various medical equipment.

The invention claimed is:

1. A method for coating an inner surface of a polyvinyl chloride medical tube containing a plasticizer, the method comprising, in the recited order, the steps of:
   passing a solution obtained by dissolving an antithrombogenic material in a solvent comprising water and at least one kind of alcohol that dissolves the copolymer but does not dissolve the plasticizer through the inner surface of the tube;
   passing water through the tube; and
   drying the tube,
   wherein an antithrombogenic material is composed of a copolymer comprising methoxypolyethyleneglycol (meth)acrylate, alkyl (meth)acrylate, and silicone(meth)acrylate,
   the solvent comprises water, ethanol, and 1-propanol in a volume ratio of 10 to 30:20 to 40:30 to 60, and
   the amount of the antithrombogenic material coating the inner surface of the tube is 1 to 500 $\mu g/cm^2$.

2. The method according to claim 1, wherein the copolymer in the solution has a concentration of 0.01 to 10 weight %.

3. The method according to claim 1, wherein the amount of the solution to be passed through the inner surface of the tube is 1 to 20% based on the gross volume of the internal cavity of the tube, and the amount of the water to be passed through the inner surface of the tube is 50 to 300% based on the gross volume of the internal cavity of the tube.

4. The method according to claim 1, wherein the solution and the water are passed through the inner surface of the tube by way of decompression suction.

5. A method for coating an inner surface of a polyvinyl chloride medical tube containing a plasticizer, the method comprising, in the recited order, the steps of:
   passing a solution obtained by dissolving an antithrombogenic material in a solvent comprising water and at least one kind of alcohol that dissolves the copolymer but does not dissolve the plasticizer through the inner surface of the tube;
   passing water through the tube; and
   drying the tube,
   wherein an antithrombogenic material is composed of a copolymer comprising methoxypolyethyleneglycol (meth)acrylate, alkyl (meth)acrylate, and silicone(meth)acrylate, and
   the amount of the solution to be passed through the inner surface of the tube is 1 to 20% based on the gross volume of the internal cavity of the tube, and the amount of the water to be passed through the inner surface of the tube is 50 to 300% based on the gross volume of the internal cavity of the tube.

6. A method for coating an inner surface of a polyvinyl chloride medical tube containing a plasticizer, the method comprising, in the recited order, the steps of:
   passing a solution obtained by dissolving an antithrombogenic material in a solvent comprising water and at least one kind of alcohol that dissolves the copolymer but does not dissolve the plasticizer through the inner surface of the tube;
   passing water through the tube; and
   drying the tube,
   wherein an antithrombogenic material is composed of a copolymer comprising methoxypolyethyleneglycol (meth)acrylate, alkyl (meth)acrylate, and silicone(meth)acrylate, and
   the amount of the antithrombogenic material coating the inner surface of the tube is 1 to 500 $\mu g/cm^2$.

* * * * *